(12) United States Patent
Fraser et al.

(10) Patent No.: US 7,060,097 B2
(45) Date of Patent: Jun. 13, 2006

(54) METHOD AND APPARATUS FOR IMPLANT STABILITY

(75) Inventors: Robert Fraser, Myrtle Bank (AU); John Riley Hawkins, Cumberland, RI (US); Christopher Rogers, Taunton, MA (US); Andrew Dooris, Fall River, MA (US); Mark Lionetto, Norton, MA (US)

(73) Assignee: DePuy Spine, Inc., Raynham, MA (US)

( * ) Notice: Subject to any disclaimer, the term of this patent is extended or adjusted under 35 U.S.C. 154(b) by 0 days.

(21) Appl. No.: 10/405,064

(22) Filed: Mar. 31, 2003

(65) Prior Publication Data

US 2004/0193271 A1 Sep. 30, 2004

(51) Int. Cl.
*A61F 2/44* (2006.01)
(52) U.S. Cl. .................... 623/17.11; 623/17.13
(58) Field of Classification Search ............. 623/17.11, 623/17.12, 17.13, 17.14, 17.15, 17.16

See application file for complete search history.

(56) References Cited

U.S. PATENT DOCUMENTS

| 5,314,477 | A | | 5/1994 | Marnay |
| 5,556,431 | A | | 9/1996 | Büttner-Janz |
| 5,800,547 | A | * | 9/1998 | Schafer et al. ............ 623/17.16 |
| 5,800,550 | A | * | 9/1998 | Sertich ..................... 623/17.16 |
| 6,113,638 | A | * | 9/2000 | Williams et al. ........... 128/898 |
| 6,193,756 | B1 | * | 2/2001 | Studer et al. ............. 623/17.15 |
| 6,416,551 | B1 | | 7/2002 | Keller |
| 6,447,544 | B1 | * | 9/2002 | Michelson ............... 623/17.16 |
| 2002/0165613 | A1 | * | 11/2002 | Lin et al. ................. 623/17.11 |
| 2003/0187506 | A1 | * | 10/2003 | Ross et al. ............... 623/17.13 |

\* cited by examiner

*Primary Examiner*—Bruce Snow
(74) *Attorney, Agent, or Firm*—Hamilton, Brook, Smith & Reynolds, PC

(57) ABSTRACT

An method and apparatus is provided for achieving stability of an implant in an intervertebral space of the human body, including an implant having a superior surface and an inferior surface, the surfaces having no significant protrusions extending therefrom and at least one modular projection mateable with one of each superior and inferior surface of the implant to achieve stability within the intervertebral space. The implants can be selected form a group of artificial discs and spinal fusion cages.

15 Claims, 15 Drawing Sheets

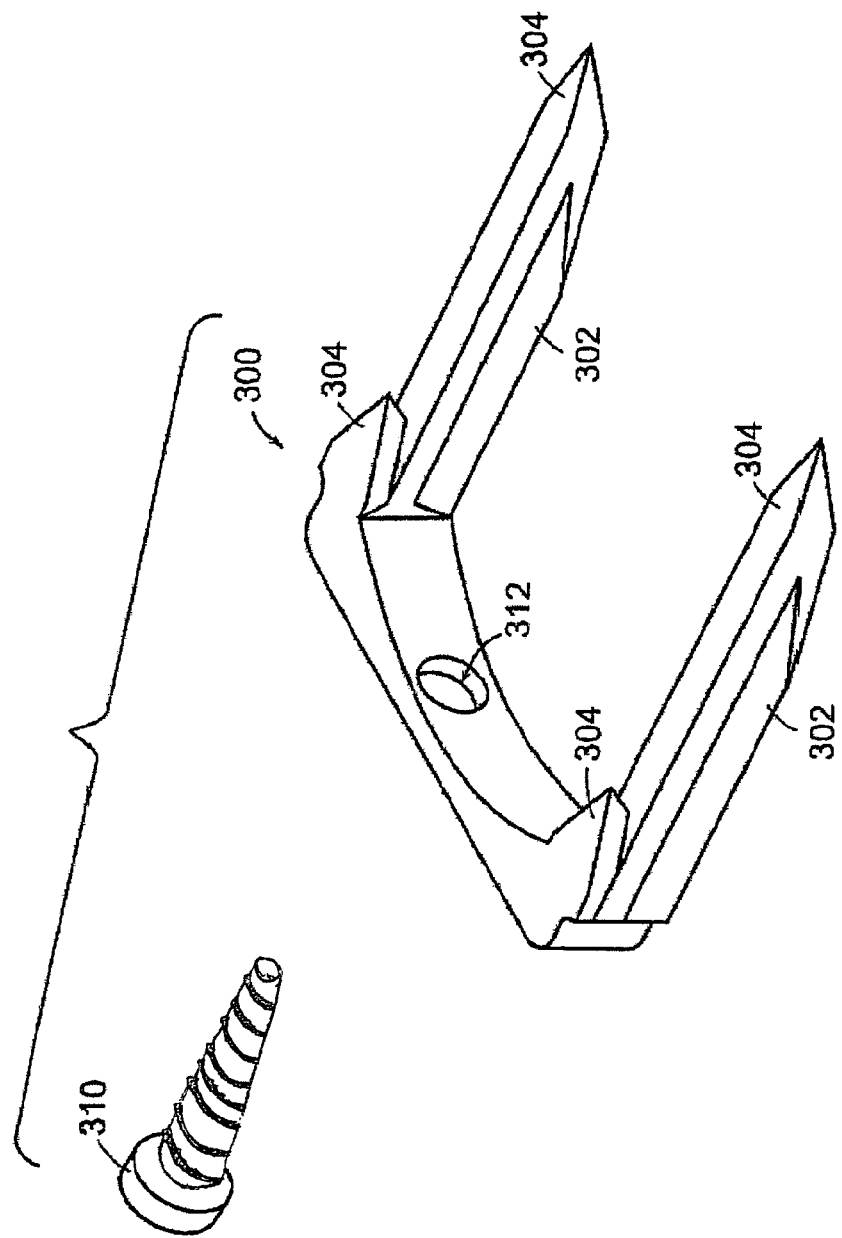

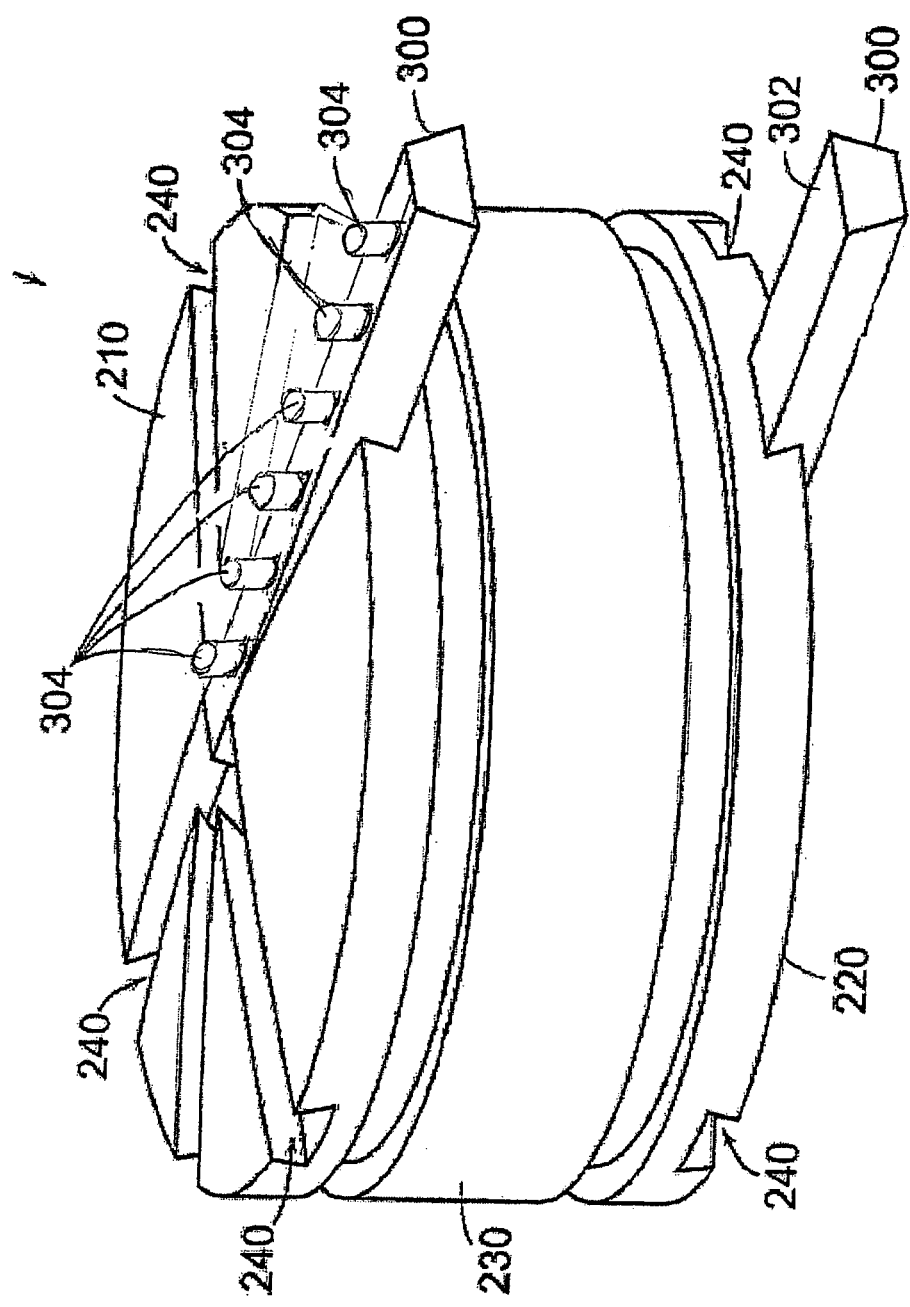

METHOD AND APPARATUS FOR IMPLANT STABILITY

BACKGROUND OF THE INVENTION

An intervertebral disc has several important functions, including functioning as a spacer, a shock absorber, and a motion unit.

The disc maintains the separation distance between adjacent boney vertebral bodies. The separation distance allows motion to occur, with the cumulative effect of each spinal segment yielding the total range of motion of the spine in several directions. Proper spacing is important because it allows the intervertebral foramen to maintain its height, which allows the segmental nerve roots room to exit each spinal level without compression.

Further, the disc allows the spine to compress and rebound when the spine is axially loaded during such activities as jumping and running. Importantly, it also resists the downward pull of gravity on the head and trunk during prolonged sitting and standing.

Furthermore, the disc allows the spinal segment to flex, rotate, and bend to the side, all at the same time during a particular activity. This would be impossible if each spinal segment were locked into a single axis of motion.

An unhealthy disc may result in pain. On way a disc may become unhealthy is when the inner nucleus dehydrates. This results in a narrowing of the disc space and a bulging of the annular ligaments. With progressive nuclear dehydration, the annular fibers can crack and tear. Further, loss of normal soft tissue tension may allow for a partial dislocation of the joint, leading to bone spurs, foraminal narrowing, mechanical instability, and pain.

Lumbar disc disease can cause pain and other symptoms in two ways. First, if the annular fibers stretch or rupture, the nuclear material may bulge or herniate and compress neural tissues resulting in leg pain and weakness. This condition is often referred to as a pinched nerve, slipped disc, or herniated disc. This condition will typically cause sciatica, or radiating leg pain as a result of mechanical and/or chemical irritation against the nerve root. Although the overwhelming majority of patients with a herniated disc and sciatica heal without surgery, if surgery is indicated it is generally a decompressive removal of the portion of herniated disc material, such as a discectomy or microdiscectomy.

Second, mechanical dysfunction may cause disc degeneration and pain (e.g. degenerative disc disease). For example, the disc may be damaged as the result of some trauma that overloads the capacity of the disc to withstand increased forces passing through it, and inner or outer portions of the annular fibers may tear. These torn fibers may be the focus for inflammatory response when they are subjected to increased stress, and may cause pain directly, or through the compensatory protective spasm of the deep paraspinal muscles.

This mechanical pain syndrome, unresponsive to conservative treatment, and disabling to the individuals way of life, is generally the problem to be addressed by spinal fusion or artificial disc technologies.

SUMMARY OF THE INVENTION

The invention is generally related to a method and apparatus for improving implant stability within an intervertebral space. As such, there is provided a method of achieving stability of an implant in the intervertebral space of the human body including, preparing the intervertebral space for implantation, positioning an implant in the prepared intervertebral space, and inserting at least one modular projection in a superior and an inferior surface of the implant to achieve stability within the intervertebral space. The modular projections are fixed in place with a locking feature, such as a screw or a bolt, to further increase stability within the intervertebral space.

An apparatus is provided for achieving stability of an implant in an intervertebral space of the human body, including an implant having a superior surface and an inferior surface, the surfaces having no significant protrusions extending therefrom and at least one modular projection mateable with one of each superior and inferior surface of the implant to achieve stability within the intervertebral space. The implants can be selected form a group of artificial discs and spinal fusion cages.

The apparatus further includes a locking feature for fixing the modular projections in place to further increase stability within the intervertebral space, wherein the locking feature can be selected form a group of screws and bolts.

The superior surface and the inferior surface of the implants include recessed mating features for accepting modular projections therein. The recessed mating features can be selected form a group of simple slots, tapered slots, dovetail slots, and holes.

The modular projections include a proximal end for mating with a recessed mating feature of a superior or inferior surface of the implant and a distal end for mating with a superior or inferior surface of vertebral endplates. The proximal end can be selected form a group of simple rectangles, tapered rectangles, dovetails, and pegs. The distal end can be selected form a group of keels, spikes, teeth, pegs, and fins.

Traditionally, spinal fusion surgery has been the treatment of choice for individuals who have not found pain relief for chronic back pain through conservative treatment (such as physical therapy, medication, manual manipulation, etc), and have remained disabled from their occupation, from their activities of daily living, or simply from enjoying a relatively pain-free day-to-day existence. While there have been significant advances in spinal fusion devices and surgical techniques, it is difficult to attain initial implant stability and subsequent manipulation.

The artificial disc offers several theoretical benefits over spinal fusion for chronic back pain, including pain reduction and a potential to avoid premature degeneration at adjacent levels of the spine by maintaining normal spinal motion. However, like spinal fusion surgery, it is difficult to attain initial implant stability and subsequent manipulation. Currently there are at least four known types of artificial discs. These artificial discs are known as the Charité, Prodisc, Marverick, and Acroflex.

The Charité achieves initial implant stability with a series of teeth positioned on the posterior and anterior sides of both superior and inferior surfaces of its endplates. The teeth are integral to the endplates, as such the disc space must be over-distracted to accommodate these projections during insertion. The Prodisc and Marverick achieve initial stability with a central keel on both superior and inferior surfaces of its endplates. The keels are integral to the endplates, as such a path must be cut into the vertebral endplates to accommodate the keels prior to implantation. The Acroflex achieves initial stability with a series of fins on both superior and inferior surfaces of its endplates positioned in an anterior-to-posterior direction. The fins are integral to the endplates, as such the fins cut small paths into the vertebral endplates as the disc is inserted during implantation. Once the Charité, Prodisc, Marverick, and Acroflex are initially positioned it is extremely difficult, if not impossible, for subsequent manipulation.

Thus, there remains a need for an improved apparatus and technique for initial artificial disc stability and subsequent manipulation. The present application is directed to those needs.

The present invention relates generally to an apparatus and technique for securing an implant between two adjacent vertebra segments. The apparatus and technique of the present invention have particular application, but are not limited to, direct anterior or oblique-anterior approaches to the spine.

BRIEF DESCRIPTION OF THE DRAWINGS

FIG. 12A is a perspective view of one embodiment of a screw 310;

FIG. 12D is a perspective view of one embodiment of a peg 304.

DETAILED DESCRIPTION OF THE INVENTION

Figure 1:
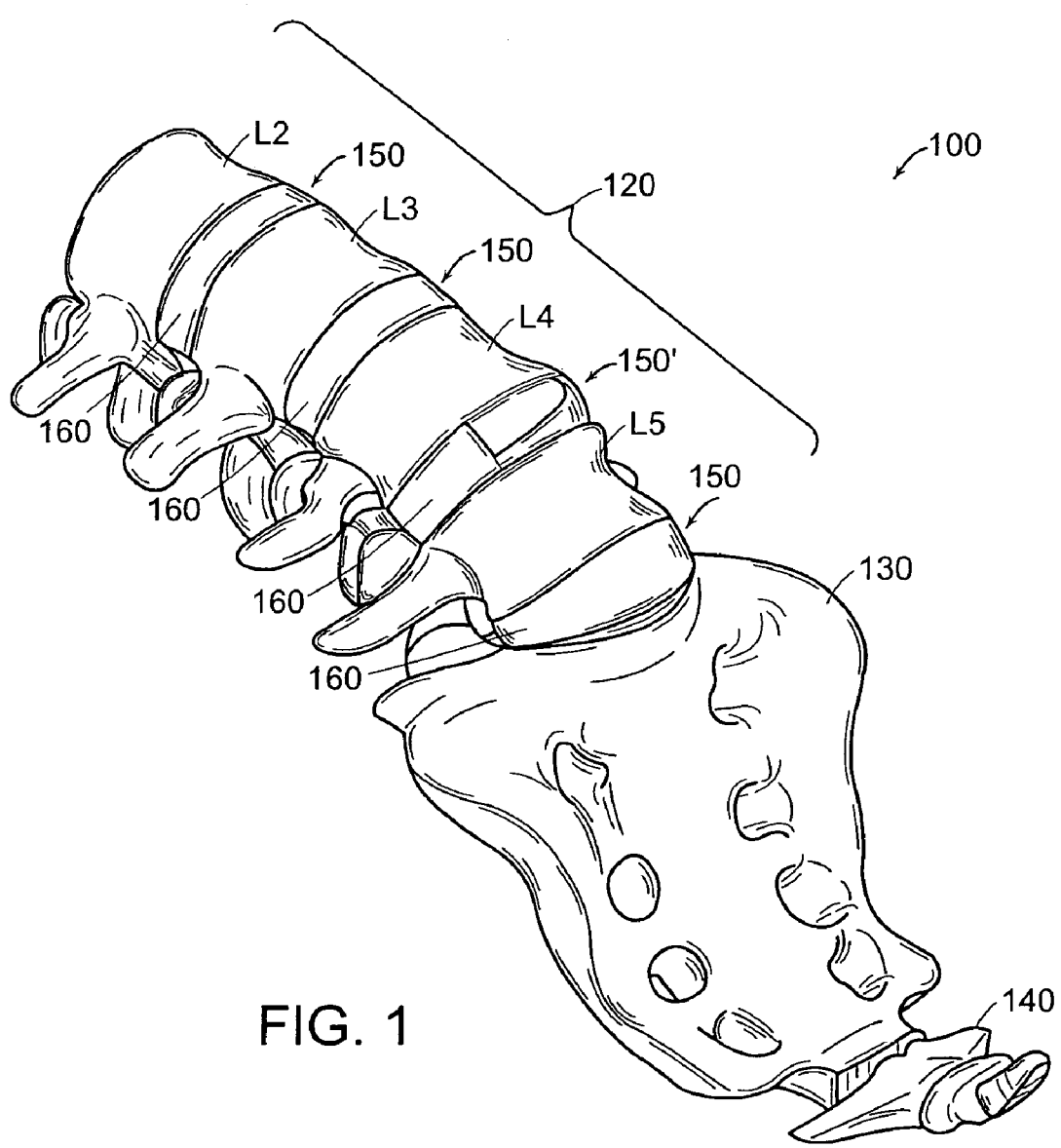
FIG. 1 is a perspective view of the lower spine, highlighting a surgically prepared disc space.

The foregoing and other objects, features and advantages of the invention will be apparent from the following more particular description of preferred embodiments of the invention, as illustrated in the accompanying drawings in which like reference characters refer to the same parts throughout the different views. The same number appearing in different drawings represent the same item. The drawings are not necessarily to scale, emphasis instead being placed upon illustrating the principles of the invention.

In general, the surgical procedure for implantation utilizes an anterior approach. During the surgery, a small incision is made in the abdomen below the belly button. The organs are carefully moved to the side so the surgeon can visualize the spine. The surgeon then removes a portion of a damaged disc. The implant is inserted into the into the intervertebral space. The implant stays in place from the tension in spinal ligaments and the remaining part of the annulus of the disc. In addition, compressive forces of the spine keep the implant in place. A successful implantation is governed by good patient selection, correct implant selection, and proper implant positioning.

FIG. 1 shows a perspective view of the lower region of the spine 100. This region comprises the lumbar spine 120, the sacral spine 130, and the coccyx 140. The lumbar spine 120 is comprised of five (5) vertebrae L5, L4, L3, L2, and L1 (not shown). Intervertebral discs 150 link contiguous vertebra from C2 (not shown) to the sacral spine 130, wherein a single quotation (') denotes a damaged disc, such as 150'.

An intervertebral disc 150 is comprised of a gelatinous central portion called the nucleus pulposus (not shown) and surrounded by an outer ligamentous ring called the annulus fibrosus 160. The nucleus pulposus is composed of 80–90% water. The solid portion of the nucleus is Type II collagen and non-aggregated proteoglycans. The annulus fibrosus 60 hydraulically seals the nucleus, and allows intradiscal pressures to rise as the disc is loaded. The annulus 160 has overlapping radial bands which allow torsional stresses to be distributed through the annulus under normal loading without rupture.

The annulus 160 interacts with the nucleus. As the nucleus is pressurized, the annular fibers prevent the nucleus from bulging or herniating. The gelatinous nuclear material directs the forces of axial loading outward, and the annular fibers help distribute that force without injury.

Although the following procedure is explained with reference to the lower spine, the procedure can be performed on any damaged disc of the spine. Further, the following procedure is described with reference to artificial discs. However, it should be understood by one skilled in the art that any implant may be used, such as a spinal fusion cage.

The damaged disc 150' is prepared to receive the artificial disc by removing a window the width of the artificial disc to be implanted from the annulus 160 of the damaged disc 150'. The nucleus pulposus of the disc 150' is completely removed.

Figure 2:
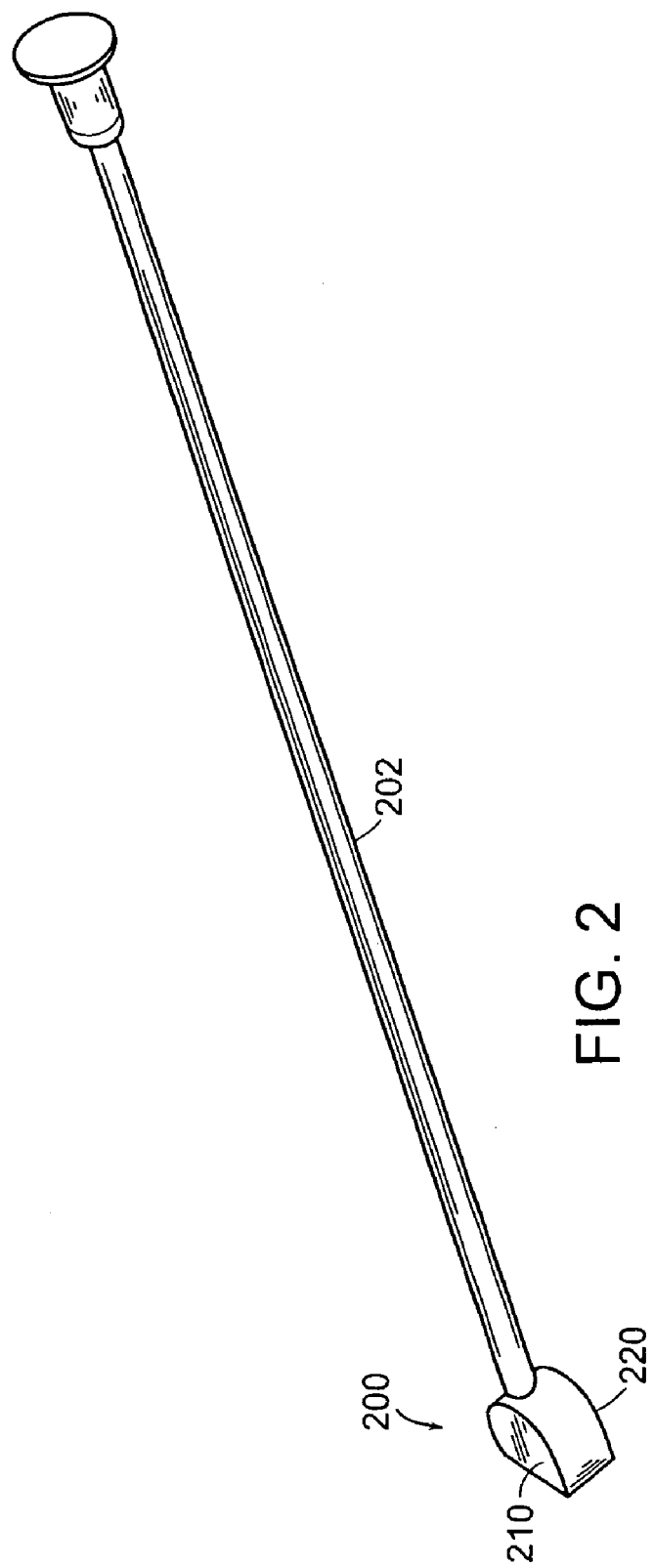
FIG. 2 is a perspective view of an artificial disc attached to an artificial disc insertion instrument.
Figure 3:
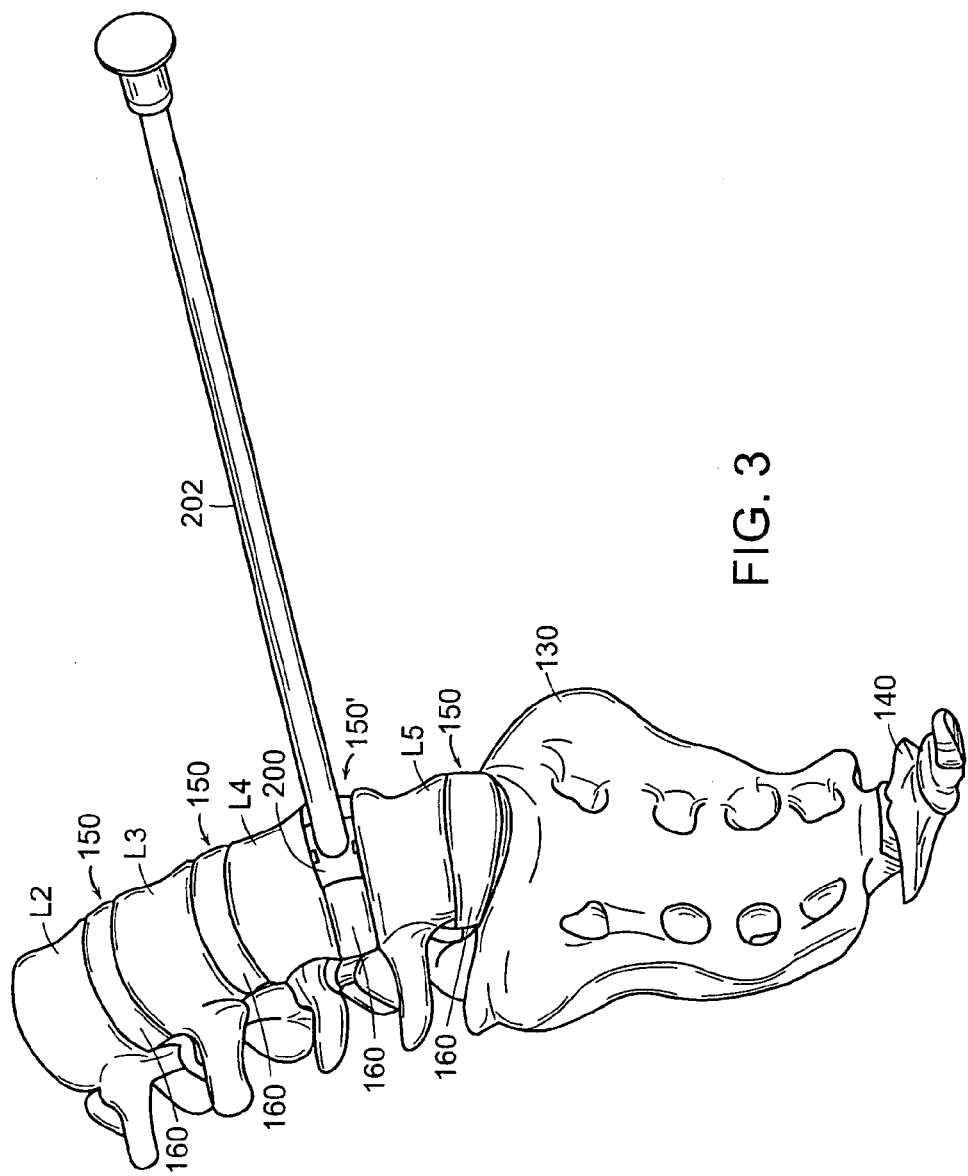
FIG. 3 is a perspective view of the artificial disc inserted into the disc space.
Figure 4:
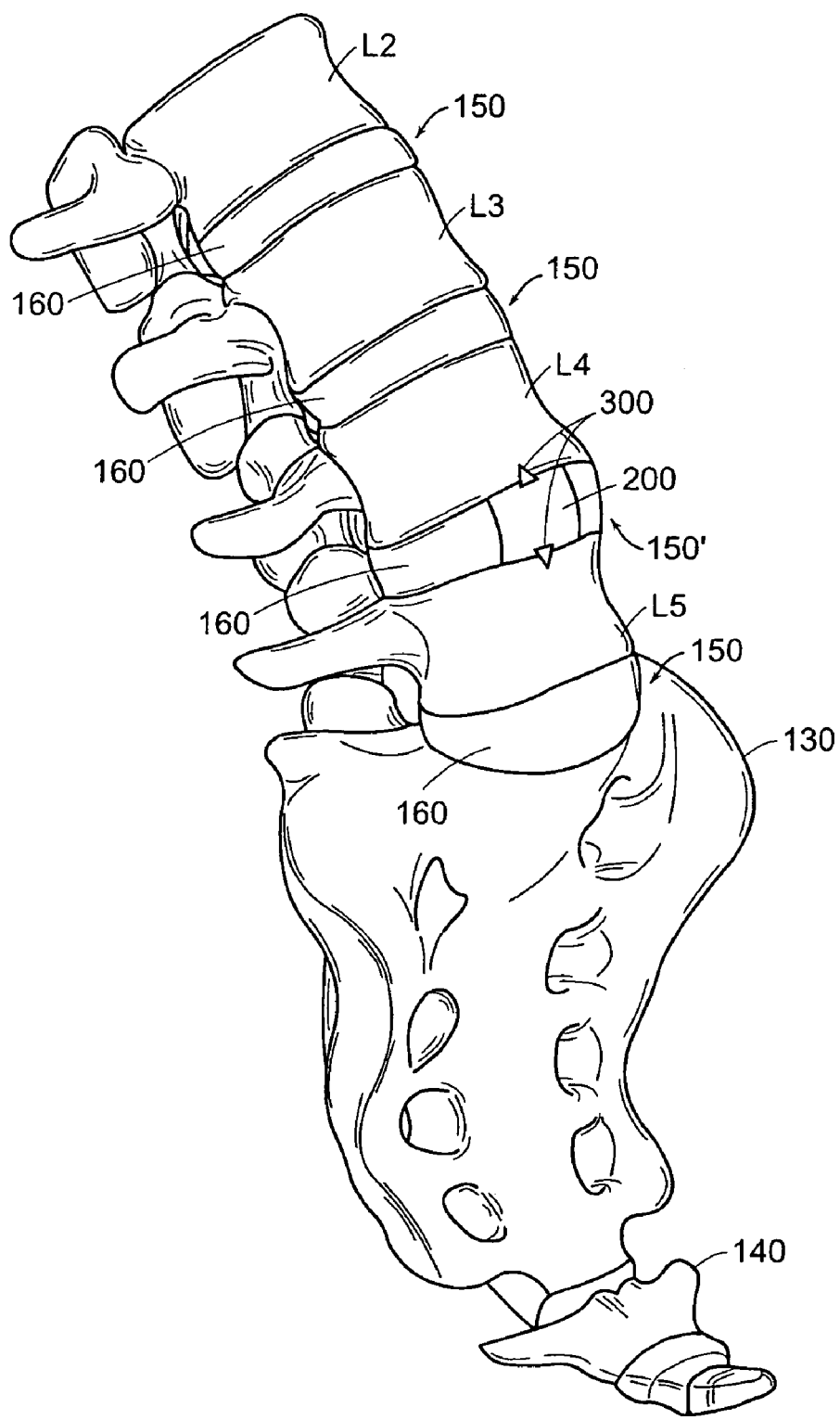
FIG. 4 is a perspective view of the artificial disc secured within the intervertebral space.

Referring to FIGS. 2–4, once the damaged disc space is prepared, the surgeon chooses an artificial disc 200 from a kit of artificial discs (not shown). The kit contains artificial discs 200 of various heights, shapes, and sizes. The surgeon inserts the chosen disc 200 into the intervertebral space and determines if the disc 200 closely matches the intervertebral space. The disc 200 may be inserted by hand or with an insertion instrument 202. If the disc 200 does not closely match the intervertebral space, the surgeon removes the disc 200 and chooses another artificial disc 200 from the kit. This step is repeated until the surgeon determines the artificial disc 200 which closely matches the intervertebral space.

The surgeon may then adjust the position of the artificial disc 200 in the intervertebral space if needed. The artificial disc can be adjusted in any direction within the axial plane of the intervertebral space. The artificial disc 200 is now ready to be secured to vertebral endplates.

At least one modular protrusion 300 is inserted into the superior and inferior endplates 210, 220 of the artificial disc 200 to secure the disc 200 to vertebral endplates. The modular protrusion 300 includes a mating feature and a securing feature. The mating feature attaches to recessions within the superior and inferior endplates 210, 220. The securing feature engages the vertebral endplates and secures the artificial disc 200 within the intervertebral space.

Figure 5:
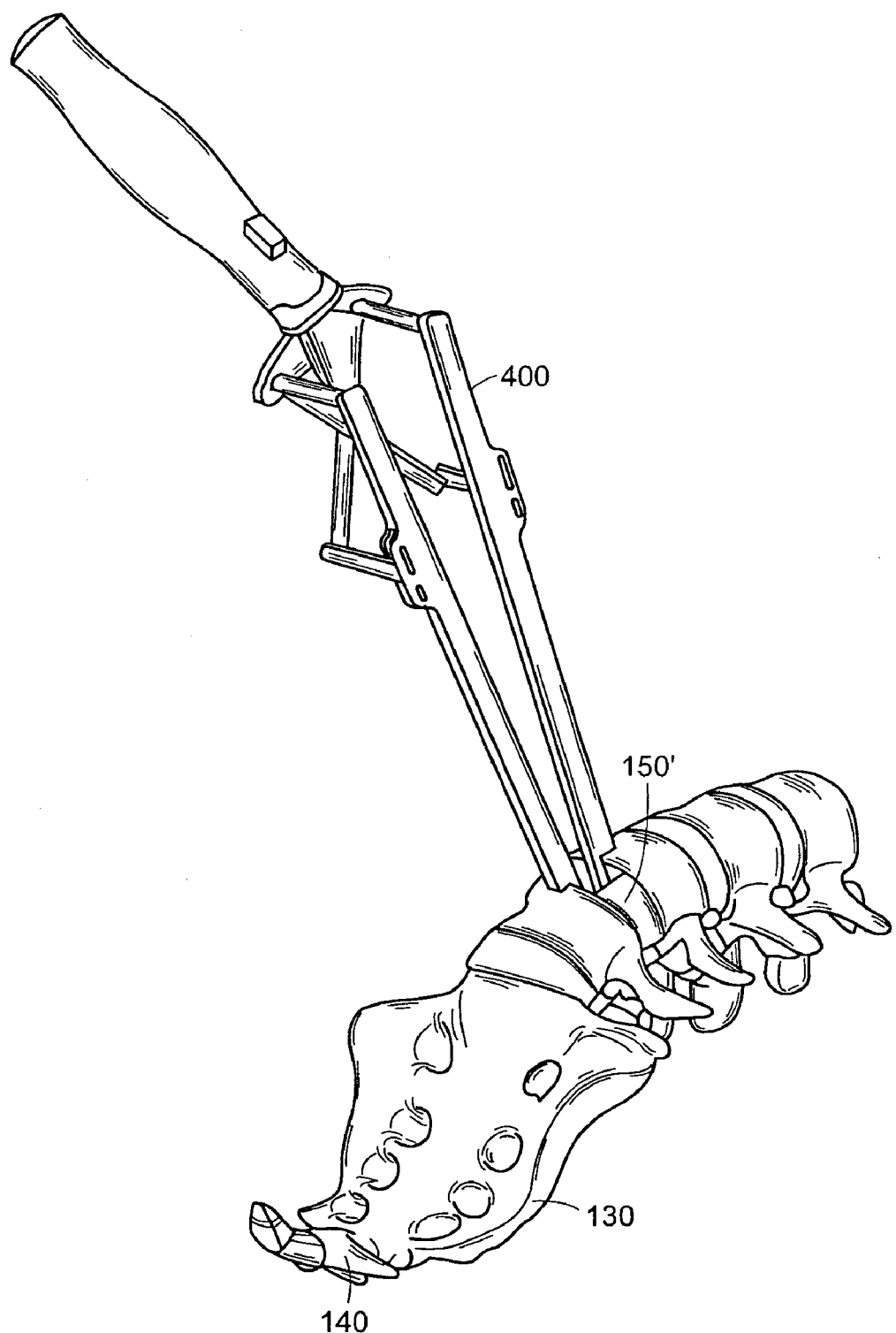
FIG. 5 is a perspective view of a distraction instrument inserted into the disc space of the lower spine.
Figure 6:
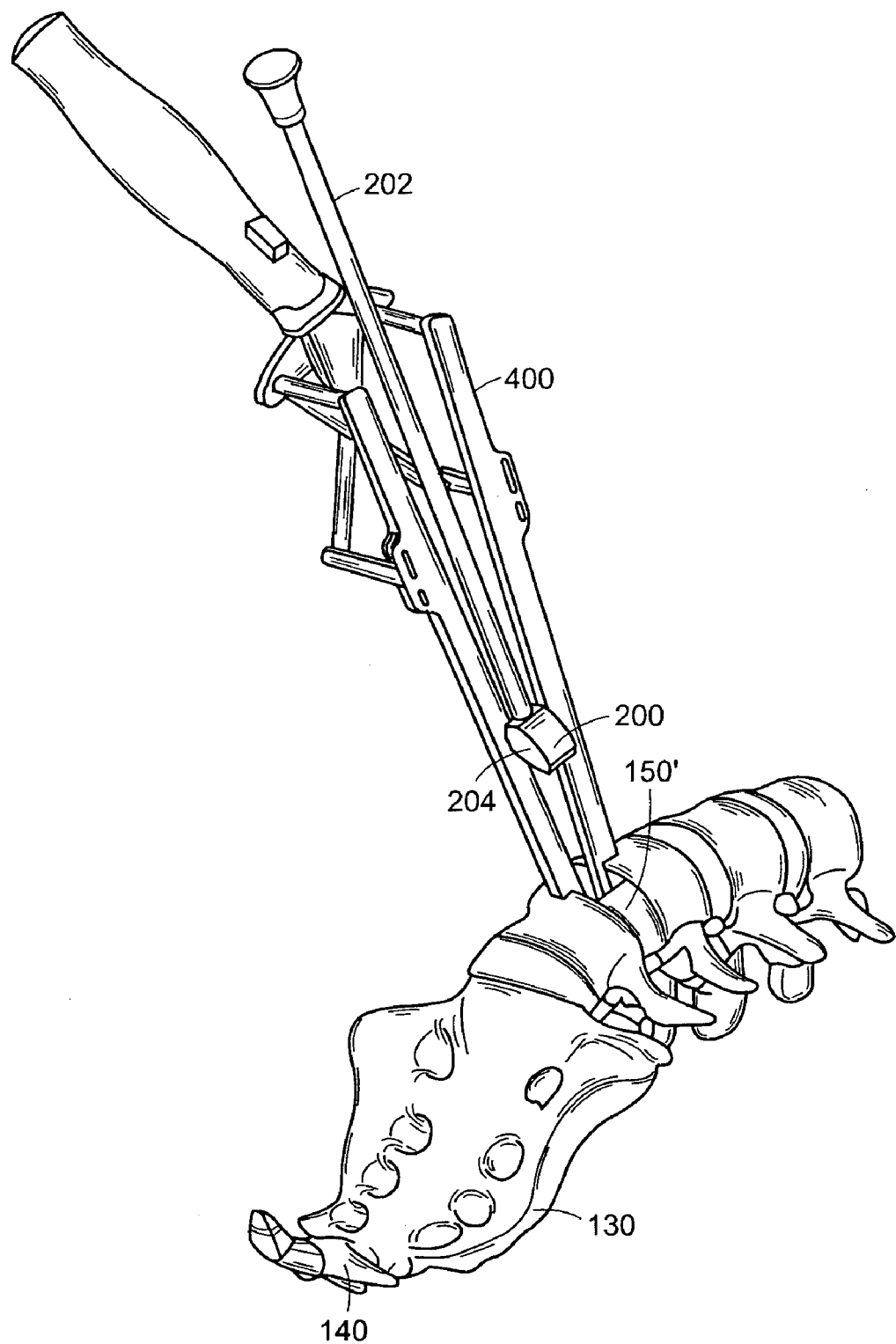
FIG. 6 is a perspective view of the artificial disc being inserted into the disc space using the distraction instrument as a guide.
Figure 7A:
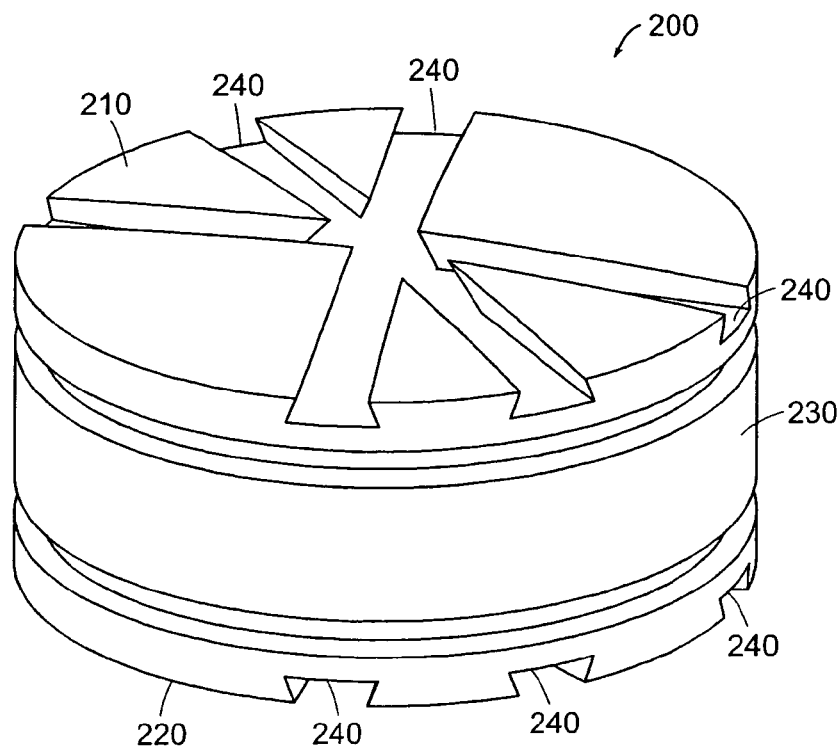
FIG. 7A is a perspective view of one embodiment of an artificial disc of the present invention.
Figure 7B:
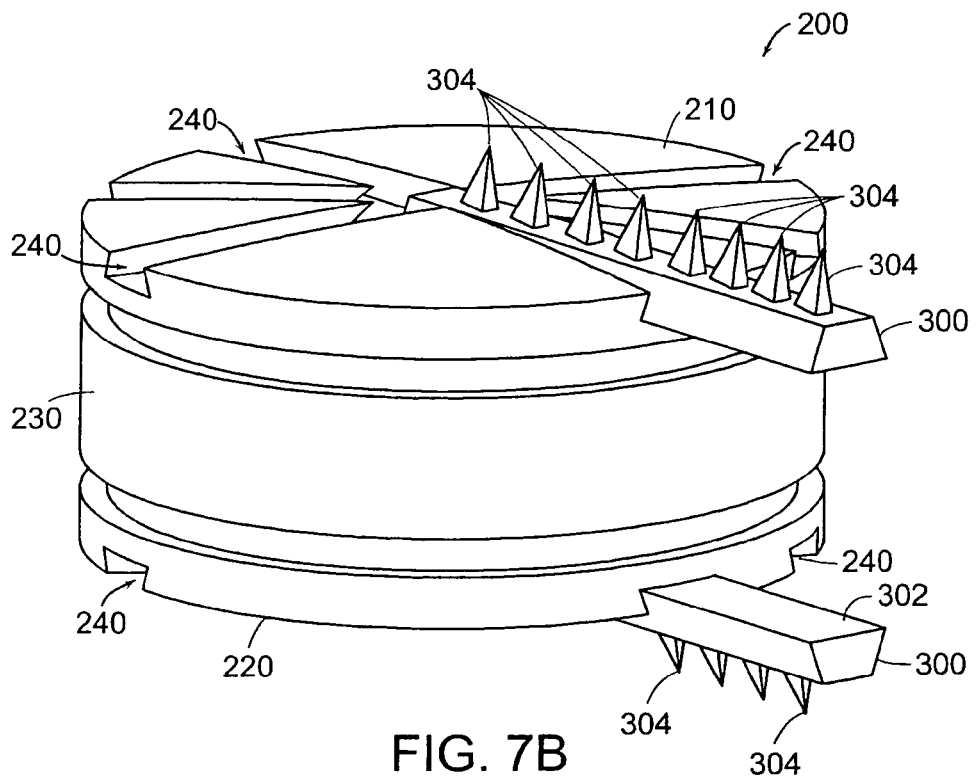
FIG. 7B is a perspective view of the artificial disc of FIG. 7A accepting one embodiment of a modular projection.
Figure 7C:
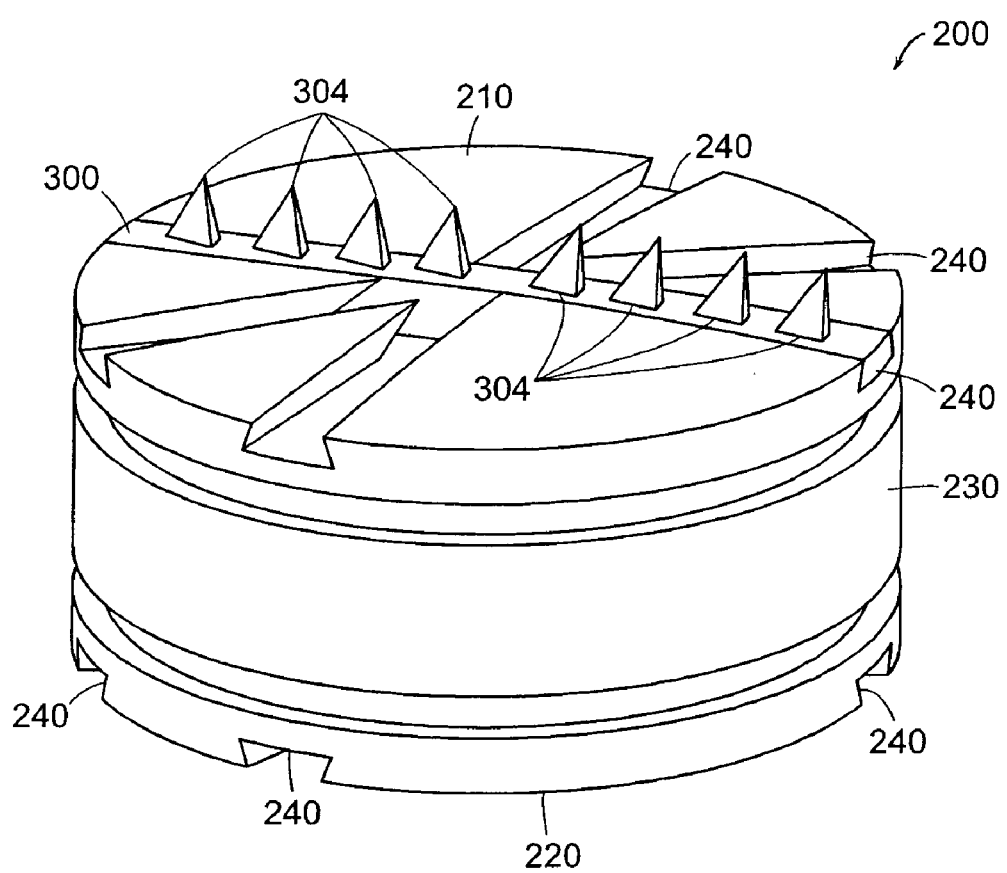
FIG. 7C is a perspective view of the artificial disc of FIG. 7A with the modular projections frilly inserted in the artificial disc.
Figure 8A:
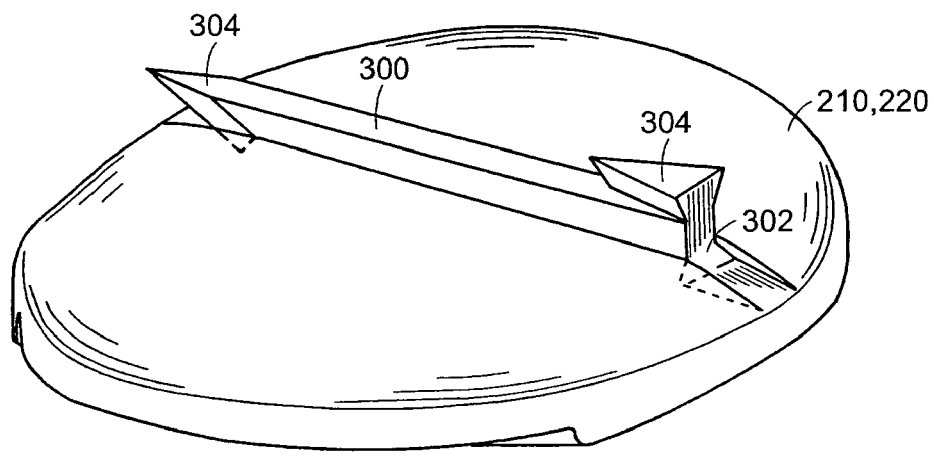
FIG. 8A is a perspective view of another embodiment of a modular projection invention fully inserted to an artificial disc endplate.
Figure 8B:
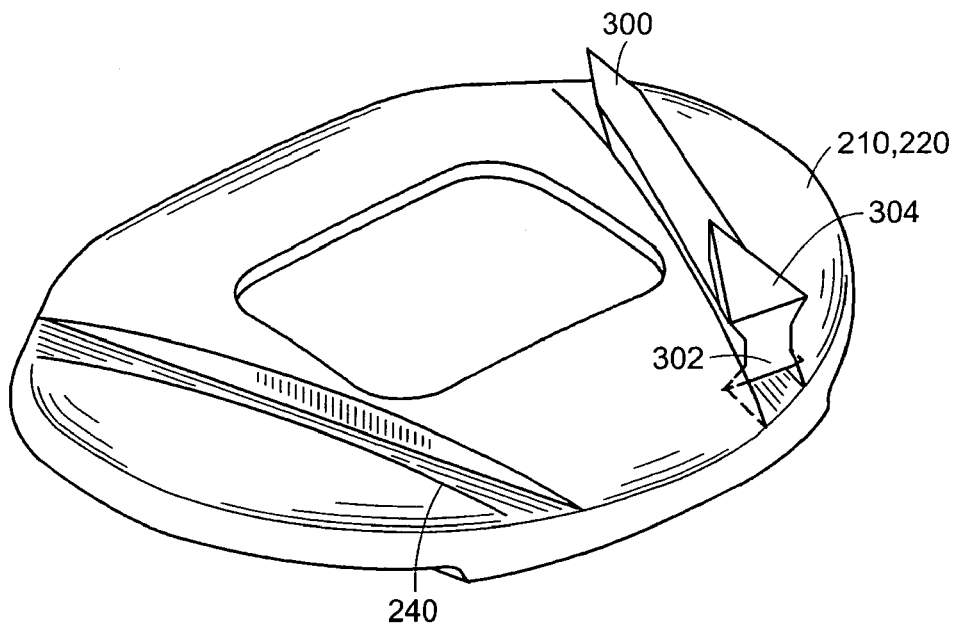
FIG. 8B is a perspective view of another embodiment of the artificial disc endplate of FIG. 8A.
Figure 9:
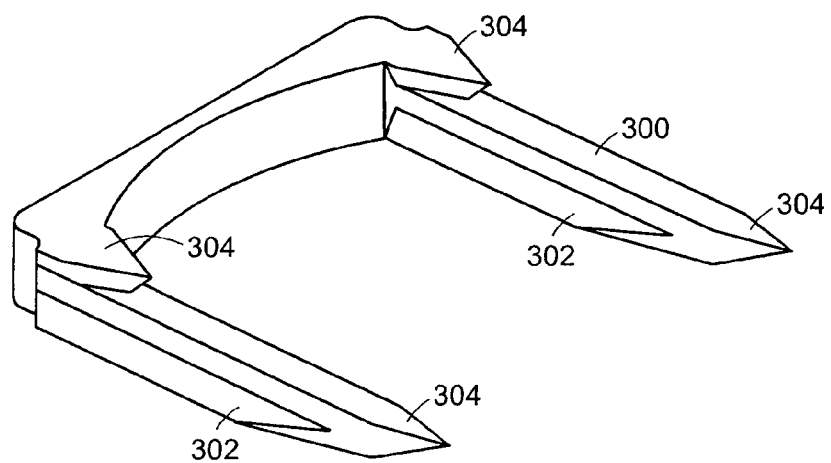
FIG. 9 is a perspective view of another embodiment of modular projection of the present invention.

Referring to FIGS. 5 and 6, in some instances the intervertebral space collapses after removal of the nucleus pulposus from the damaged disc 150'. Thus, the surgeon may not be able to effectively insert the artificial disc 200 into the intervertebral space. Therefore, the intervertebral space can be distracted using a distraction instrument 400. The distraction instrument 400 is inserted into the intervertebral space and engaged to distract the intervertebral space to a height which will enable the surgeon to insert the artificial disc 200 into the intervertebral space. The artificial disc 200 is inserted into the intervertebral space using the distraction instrument 400 as a guide. This procedure is repeated if necessary as explained above.

Referring to FIGS. 7A–10, the artificial disc 200 includes a superior endplate 210, an interior endplate 220, and a flexible core 230 between the superior and interior endplates 210, 220. The surfaces of the endplates should contain relatively small, if any, projections therefrom. The endplates 210, 220 include recessed mating features 240 for accepting modular projections 200. The recessed mating features 240 may be of any type of mating feature known in the art, such as simple slots, tapered slots, dovetail slots, and holes. The recessed mating feature 240 may also be used to accept mating features of the implant insertion instrument 202.

The modular projections 300 include a mating feature 302 and a securing feature 304. The mating feature 302 may be of any type of mating feature known in the art, such as a simple rectangle, a tapered rectangle, a dovetail, and a pin. The mating feature 302 should match the recessed mating feature 240 of endplates 210, 220. The securing feature 304 may be of any type of securing feature known in the art, such as a keel, a spike, a tooth, teeth, a peg, and a fin. The securing feature 304 engages the vertebral endplates and secures the artificial disc within the intervertebral space.

Figure 10:
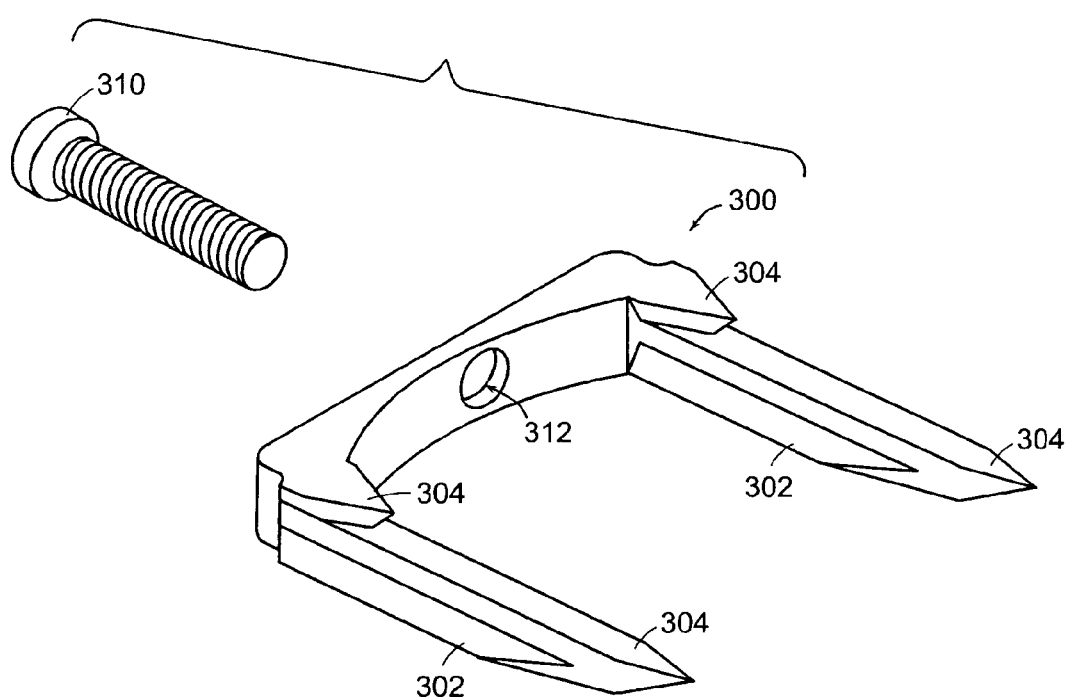
FIG. 10 is a perspective view of one embodiment of a locking mechanism for the modular projection of FIG. 9.

The artificial disc can be further secured within intervertebral space by a locking feature 310 (FIG. 10). The locking feature 310 secures the modular projection 300 to the artificial disc 200 through hole 312. The locking feature 304 may be of any type of locking feature known in the art, such as a screw, and a bolt.

Figure 11A:
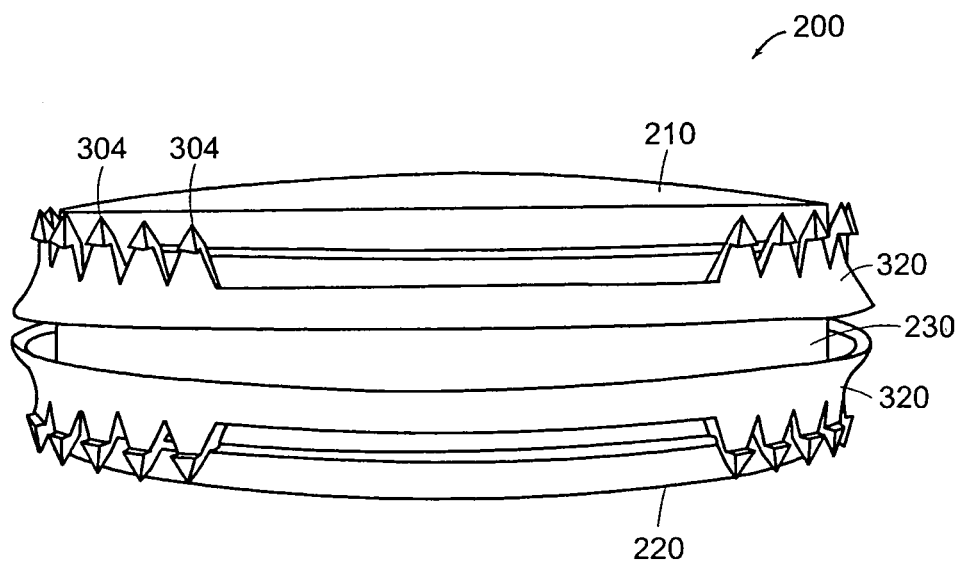
FIG. 11A is a perspective view of an alternative embodiment of the present invention in a closed position.
Figure 11B:
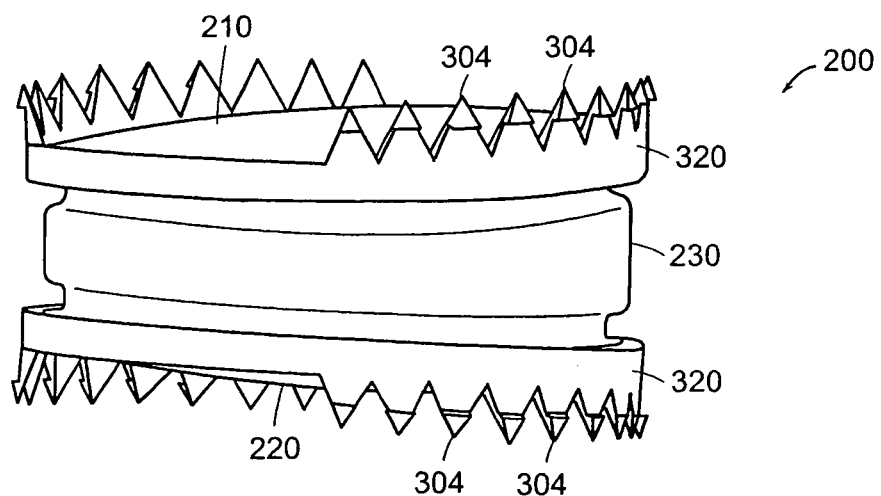
FIG. 11B is a perspective view of the alternative embodiment of FIG. 11A in an open position.
Figure 12B:
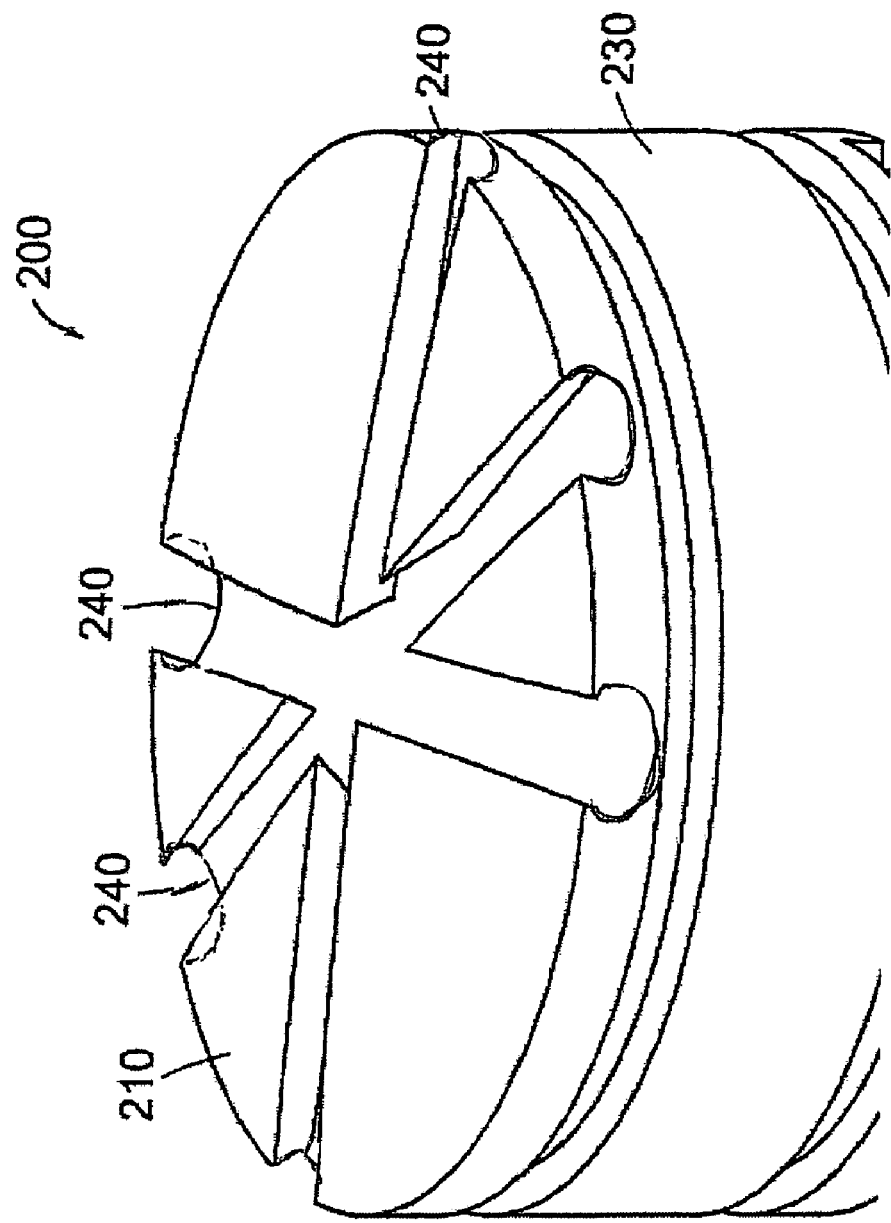
FIG. 12B is a perspective view of one embodiment of a hole 240.
Figure 12C:
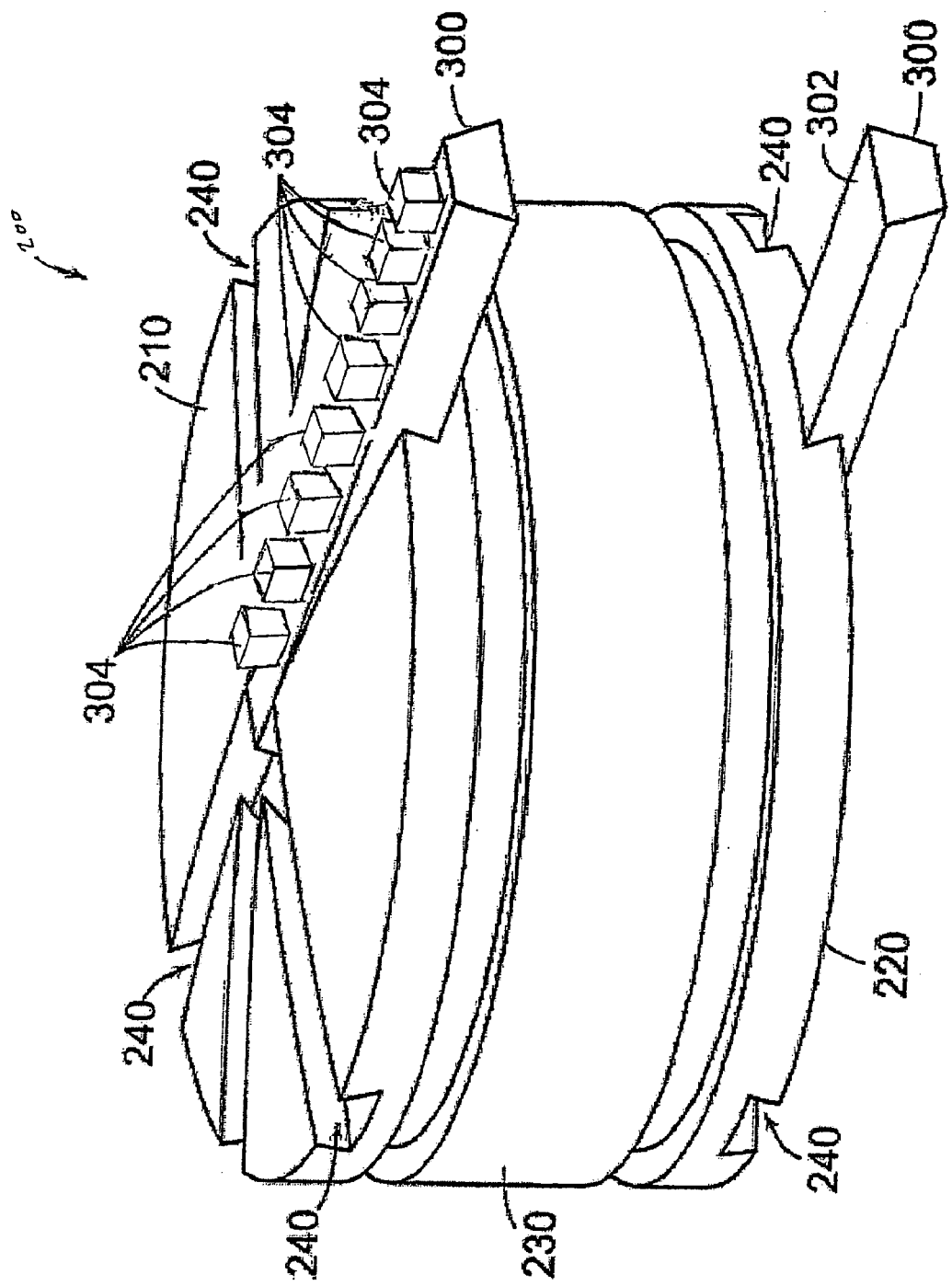
FIG. 12C is a perspective view of one embodiment of a rectangle 304.

FIGS. 11A and 11B illustrate an alternative embodiment of the invention. The modular projection 300 is slidable about the circumference of the artificial disc 200. In a closed position (FIG. 11A), the securing features 304 of the modular projections 300 do not extend pass the surface of the endplates 210, 220. However, in an open position (FIG. 11B), the securing feature 304 of modular projections 300 engages the vertebral endplates and secures the artificial disc within the intervertebral space.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of achieving stability of an implant in an intervertebral space of the human body, comprising:
   (a) preparing the intervertebral space for implantation;
   (b) positioning an implant in the prepared intervertebral space, the implant including a superior endplate, an inferior endplate, and a flexible core disposed between the endplates, whereby an exterior surface of each endplate engages a respective vertebral endplate and each endplate defines at least one elongated channel, wherein a longitudinal axis of the channel is substantially parallel to a surface of the endplate; and
   (c) inserting at least one modular projection in and along the longitudinal axis of the elongated channel in each of the superior and inferior endplates of the implant to achieve stability within the intervertebral space.

2. The method of claim 1, wherein the implant includes at least one member selected from the group consisting of artificial discs and spinal fusion cages.

3. The method of claim 1, wherein the modular projection is fixed in place with a locking feature to further increase stability within the intervertebral space.

4. The method of claim 3, wherein the locking feature includes at least one member selected from the group consisting of screws and bolts.

5. The method of claim 1, wherein the elongated channel is defined by at least one member selected from the group consisting of a simple slot, a tapered slot, a dovetail slot, and a hole.

6. The method of claim 1, wherein the modular projection includes,
   (a) a proximal end for mating with the elongated channel of a superior or inferior endplate of the implant; and
   (b) a distal end for mating with a corresponding superior or inferior surface of a vertebral endplate.

7. The method of claim 6, wherein the proximal end includes at least one member selected from the group consisting of simple rectangles, tapered rectangles, dovetails, and pegs.

8. The method of claim 6, wherein the distal end includes at least one member selected from the group consisting of keels, spikes, teeth, pegs, and fins.

9. The method of claim 1, wherein at least two modular projections are inserted into corresponding elongated channels of each superior and inferior endplate.

10. The method of claim 1, wherein the longitudinal axes of the elongated channels of least one of the superior and inferior endplates intersect.

11. The method of claim 1, wherein the modular projection includes a cross member coupled between two engagement bodies, each engagement body mateable with a corresponding elongated channel in one of each of superior and inferior endplates of the implant.

12. The method of claim 11, wherein the cross member defines a hole for accepting a locking feature for fixing the modular projection in place to further increase stability within the intervertebral space.

13. An apparatus for achieving stability of an implant in an intervertebral space of the human body, comprising:
   (a) an implant having a superior endplate, an inferior endplate, and a flexible core disposed between the endplates, each endplate defining an exterior surface of the apparatus and further defining at least one elongated channel, wherein a longitudinal axis of the channel is substantially parallel to a surface of the endplate, wherein the longitudinal axes of at least two elongated channels of at least one of the superior and inferior endplates intersect; and (b) at least one modular projection mateable with the elongated channel in at least one of each of the superior and inferior endplates of the implant to achieve stability within the intervertebral space.

14. An apparatus for achieving stability of an implant in an intervertebral space of the human body, comprising:

(a) an implant having a superior endplate, an inferior endplate, and a flexible core disposed between the endplates, each endplate defining an exterior surface of the apparatus and further defining at least one elongated channel, wherein a longitudinal axis of the channel is substantially parallel to a surface of the endplate; and (b) at least one modular projection mateable with the elongated channel in at least one of each of the superior and inferior endplates of the implant to achieve stability within the intervertebral space, wherein the modular projection includes a cross member coupled between two engagement bodies, each engagement body mateable with a corresponding elongated channel in one of each of superior and inferior endplates of the implant.

15. The apparatus of claim 14, wherein the cross member defines a hole for accepting a locking feature for fixing the modular projection in place to further increase stability within the intervertebral space.

* * * * *